United States Patent [19]
Simon

[11] 3,943,753
[45] Mar. 16, 1976

[54] SOLID STATE VISCOSIMETER
[75] Inventor: Frank N. Simon, Bloomington, Minn.
[73] Assignee: Honeywell Inc., Minneapolis, Minn.
[22] Filed: June 17, 1974
[21] Appl. No.: 479,727

[52] U.S. Cl.......................................... 73/54; 73/59
[51] Int. Cl.²........................................ G01N 11/16
[58] Field of Search................... 73/54, 59, 32 A

[56] References Cited
UNITED STATES PATENTS

| | | | |
|---|---|---|---|
| 2,340,992 | 2/1944 | Siegel | 73/59 |
| 2,707,391 | 5/1955 | McSkimin | 73/59 |
| 2,839,915 | 6/1958 | Roth et al. | 73/59 |
| 3,062,040 | 11/1962 | McKennell et al. | 73/59 |

FOREIGN PATENTS OR APPLICATIONS

| | | | |
|---|---|---|---|
| 830,463 | 3/1960 | United Kingdom | 73/59 |

Primary Examiner—Richard C. Queisser
Assistant Examiner—Joseph W. Roskos
Attorney, Agent, or Firm—Theodore F. Neils; Omund R. Dahle

[57] ABSTRACT

A viscosimeter is provided using a piezoelectric transformer to provide vibratory energy thereby imparting shear waves to the surrounding fluid. An output signal provides a representation of the fluid viscosity.

11 Claims, 2 Drawing Figures

SOLID STATE VISCOSIMETER

BACKGROUND OF THE INVENTION

This invention relates to viscosimeters which provide a representation of the viscosity of those fluid portions adjacent to the viscosimeter and particularly to viscosimeters wherein a transducer is used to determine this viscosity by its imparting shear waves to the adjacent fluid portions.

Various viscosimeters using members in motion to impart shear waves to fluids to determine the viscosity thereof have been devised heretofore. Among them is a viscosimeter in which a cup, suspended by wires, is driven in a rotational oscillation of the cup to provide an indication of the viscosity of the fluid. This viscosimeter requires rather an elaborate mechanical arrangement and typically uses an elaborate electrical arrangement utilizing a feedback loop from one suspension wire to the driver which loop includes amplification and other operations on the signals involved.

Another viscosimeter utilizes a pair of rectangular bars, one of the bars at least being of a piezoelectric material, with the fluid of interest located therebetween. The piezoelectric bar receives shear waves transmitted through the fluid by the other bar when this other bar is driven in reciprocating, oscillatory motion in its direction of elongation. The motion of the piezoelectric bar as a result of the shear waves impinging thereon is an indication of the viscosity of the fluid, this motion being converted into an electrical output by the transduction of energy from one form to another occurring in the piezoelectric bar. Again, a rather elaborate mechanical arrangement is required. A rather small output signal is obtained which usually must be amplified in the electrical output circuit for the signal to be satisfactorily used.

A viscosimeter which, in mechanical principles, is somewhat simpler than the foregoing viscosimeters is based on an electrically driven, torsionally vibration, cylindrical piezoelectric crystal. These torsional vibrations impart primarily shear waves to those fluid portions adjacent to the crystal with use of a properly designed crystal. The effects of the fluid at the surface of the vibrating crystal provides a damping force on the crystal, i.e., the loading thereon. Therefore, as the viscosity changes and so the damping at the crystal's surface, the effective input impedance seen at the electrical driving terminals of the crystal also changes. The effective electrical input impedance can be analytically derived from an equivalent electrical circuit which includes in its generalized impedances the mechanical effects of both the torsionally vibrating crystal and the fluid. Viscosity can be determined through measuring the input impedance at the crystal resonance frequency with another calibration measurement of the input impedance with the crystal submerged in a fluid of known parameters. This impedance measurement, however, is a rather inconvenient measurement.

SUMMARY OF THE INVENTION

A viscosimeter is provided in which a piezoelectric transformer has surfaces placed in motion in directions such that shear waves are imparted to those portions of the fluid of interest adjacent to these surfaces. This transducer has electrical input terminals to which oscillator circuitry means are attached. The transducer has output terminals which provides an output voltage signal at the resonant frequency of the submerged transformer. This output signal may be used with a display and/or computational means or other output sensing means.

With the viscosimeter at least partially submerged in a fluid of interest, the output signal is related to the fluid viscosity and the fluid density for adjacent fluid portions. In general, the viscosity measured will be the effective viscosity of the fluid for the level of shear stress applied. For the simplest of viscous fluids, Newtonian fluids, the measured viscosity will be the Newtonian viscosity parameter which is independent of the applied shear stress. Further fluid parameters may be measured in more complex fluids to aid in providing a representation of a Newtonian fluid viscosity parameter for the fluid of interest.

DESCRIPTION OF THE PREFERRED EMBODIMENTS

Figure 1:
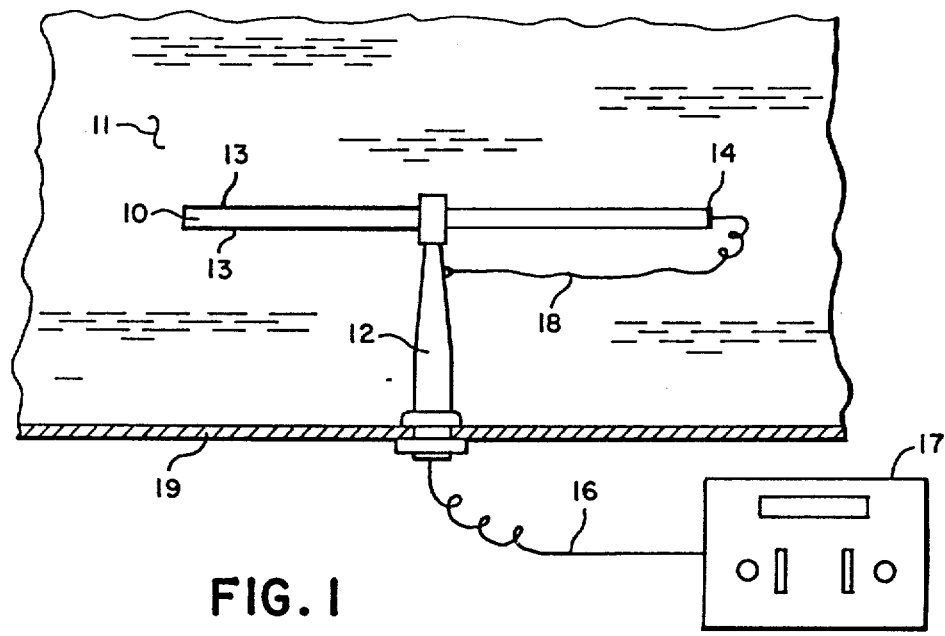
FIG. 1 shows one embodiment of the present invention.

Under a shear stress, all fluids exhibit a viscosity which is due to momentum transfer between various portions of the fluid. If the fluid was such that upon application of a shear stress there results a rate of change of shear strain which is a linear function of, i.e. proportional to, the applied shear stress, the fluid is termed a Newtonian fluid and the constand of proportionality is the Newtonian viscosity. Such a fluid behavior is characteristic typically of gases and many liquids, at least in a range of conditions.

However, many liquids exhibit more complicated behavior, as probably do all fluids in extreme conditions, with the rate of change of shear strain being a more complicated function of the applied shear stress. In these cases the function giving the dependence of the rate of change of shear strain on the applied stress will typically contain a term which is linear in the applied shear stress, representing the Newtonian portion of the behavior of the fluid and its Newtonian viscosity, and will also contain other terms which are more complicated functions of the applied shear stress which considered together can be used to define fluid viscosity. This fluid viscosity is the ratio of the rate of change of shear strain to the applied shear stress evaluated for the actual shear stress applied. As a result, fluid parameters other than Newtonian viscosity in these fluids will be important in determining the rate of change of shear strain as a function of applied shear stress, such as shear elasticity and the viscoelastic coefficient, parameters due to shear thickening and thinning, etc.

When a vibrating body is provided in a fluid, the vibratory motion of the body can generally apply both shear stresses and normal stresses to the fluid. The applied shear stresses, with the resulting rate of change of shear strain related thereto as indicated above, and the applied normal stresses lead to acoustic waves occurring in the fluid, both shear waves and longitudinal waves. The reactive force of the fluid on the vibrating body loads the body, dampening its motions, with the result that the vibratory characteristics of the body are altered. This reactive force of the fluid must be equaled by the force in the stresses applied to the fluid by the vibrating body.

The fluid reactive shear force, being the shear stress of the fluid integrated over the surface area of the vibrating body, is related to the rate of change of shear strain by the fluid parameters discussed above relating shear stress and rate of change of shear strain. This relationship between the altered vibrating body characteristics, due to the shear reactive force of the fluid thereon, and the fluid parameters provides a basis for determining some of these fluid parameters through determining the changes in parameters describing the vibrating body, these changes being the result of altering the vibrating characteristic of the body due to loading it with a fluid.

A method for using a vibrating body to determine fluids parameters, already indicated above, involves measuring the change in the effective input impedance between two electrical input terminals of an electrically driven, torsionally vibrating, cylindrical crystal which is driven by a sinusoidal electrical voltage at the same input terminal. A properly designed torsionally vibrating, cylindrical crystal will impart mostly shear wave energy to the surrounding fluid and relatively little longitudinal wave energy. This method is reported in the *Transactions of the American Society of Mechanical Engineers* for May, 1974 at page 359 thereof.

One analytical view of this method leads to representing the torsionally vibrating crystal by an equivalent "electrical" circuit, as already indicated, through use of an ideal transformer and use of generalized impedances for the elements of the equivalent circuit. Both resistive and reactive generalized impedance elements serving as radiation impedances are found to be needed to represent the torsionally vibrating crystal in the fluid of interest. This indicates that power dissipation will occur, i.e. energy will be imparted to the fluid via the shear waves initiated therein by the torsionally vibrating crystal, and that a shift in resonant frequency will occur dependent upon the values required for these generalized impedance elements to represent adequately the crystal as submerged in the fluid.

The values of these generalized impedance elements will be functions of the fluid parameters since these impedances represent the crystal as it is subjected to the shear reactive force of the fluid thereon or, from another view, the impedances represent the torsionally vibrating crystal structural parameters as modulated by the surrounding fluid to an extent determined by the parameters of the fluid which structural parameter modulation in turn modulates the acoustic vibratory energy in the crystal. The ideal transformer represents the transduction, in the torsionally vibrating crystal, from input electrical energy to acoustical vibratory energy. As these generalized radiation impedances change in value with changing fluid parameters, the effective input impedance at the electrical input terminals changes accordingly.

The measurement of the change in the effective input impedance at resonance, which impedance at resonance is purely resistive, is not a particularly convenient measurement, however. Considerably more convenient to measure would be a signal obtained more directly from the acoustic vibratory energy as modulated by the presence of the fluid.

The present invention contemplates accomplishing this by use of a piezoelectric transformer. The second transduction of energy forms which occurs therein, changing from acoustic vibratory energy to electrical energy again, provides an output electrical signal related to the modulated acoustic vibratory energy. This, from an equivalent circuit point of view is related to adding another ideal transformer to the equivalent electrical circuit described above although in choosing to use a practical piezoelectric transformer, the vibration may no longer be torsional.

FIG. 1 shows a piezoelectric transformer, 10, in the shape of a rectangular bar of piezoelectric material provided in a fluid, 11. Piezoelectric transformer 10 is shown mounted in a mount, 12, fastening the piezoelectric transformer at a location centered along its length. Transformer 10 may be constructed of a ferroelectric ceramic such as lead zirconate titanate (PZT) for instance. The width of the piezoelectric transformer which is directed perpendicular to the plane of the drawing is considerably greater than is its thickness. In this configuration, much of the surface area of the transformer when in operation will be in motion in directions which will impart shear wave energy to the fluid 11 but substantially surface portions thereof will also impart longitudinal wave energy to the fluid. Proper geometrical design of the transducer 10, such as making the geometrical form shown in FIG. 1 very thin, will maximize the amount of shear wave energy provided to the longitudinal wave energy provided.

Two electrodes, 13, the input electrodes, cover the entire portion of the length-width faces of the piezoelectric transformer to the left of mount 12 as shown in FIG. 1. These electrodes are thus separated by the thickness of the piezoelectric transformer.

A third electrode, 14, is provided at the extreme right hand end of the piezoelectric transformer, as shown. An external electrical cable, 16, leads from mount 12 to the driving and sensing electronics, 17. Cable 16 has several conductors therein which attach to the input electrodes 13 within mount 12 and which attach to output electrode 14 through a connection means, 18. A portion of the fluid container wall, 19, is shown also.

The operation of the piezoelectric transformer, 10, is that of typical piezoelectric transformer operation. An oscillatory driving voltage is applied at input terminals 13 and a stepped-up output voltage appears at terminal 14 with respect to terminals 13. Mount 12 is centered along the length of piezoelectric transformer 10 since a node in the vibratory movement of the transformer occurs at this point. This node is the result of the half wavelength resonance of the unloaded piezoelectric transformer and having each side of the transformer being equally loaded by the fluid.

Electronics 17 includes an oscillator circuit to supply voltage to input terminals 13. The oscillator electronics are such that the frequency of oscillation of the voltage applied to input terminals 13 is set by the effective input impedance occurring between input terminals 13 which impedance becomes a functional impedance in the oscillator circuit, much in the manner of a crystal controlled oscillator with piezoelectric transformer 10 being the controlling crystal. An oscillator circuit with a square wave voltage provided at the input terminals of the transformer results on a sinusoidal wave voltage at the transformer output which can be picked up by a feedback loop to form the oscillator is a particularly effective driving circuit.

The oscillation frequency of the circuit will occur at a resonant frequency of the transformer as submerged in the fluid 11, this resonant frequency being the frequency at which the effective input impedance of the transformer becomes purely resistive. Analytically, this effective input impedance is determined from the generalized impedances representing the piezoelectric transformer submerged in fluid 11 as they are reflected across the ideal input transformer representing the transduction from input electrical energy to acoustic vibratory energy. In the present embodiment there are no significant input electrical impedances on the primary side of this ideal input transformer to consider. As a result, piezoelectric transformer 10 is always at its resonant frequency as determined by both the characteristics of the transformer and the effects on the transformer of fluid 11 surrounding it.

Use of a variable frequency electrical wave generator to find the resonant frequency (at which frequency not only is the effective input impedance purely resistive but also the output voltage is at maximum amplitude) by use of a sinusoidal wave and to drive transformer 10 at this frequency when submerged is also possible but is not as convenient. The resonant frequency can be determined most conveniently in this method by monitoring the output voltage signal at terminal 14 for the submerged transformer and adjusting the wave generator frequency until this voltage signal has a maximum amplitude. Use of a square wave from the generator can eliminate any need to find the resonant frequency since the resonant frequency would substantially be the only frequency excited and present at the transformer output.

For proper operation, the shear wave energy should dissipate within the fluid 11 entirely before encountering any objects foreign to the fluid. This means no unwanted reflective surfaces belonging to foreign bodies should be near the viscosimeter nor should any other uncharacteristic fluid discontinuites be allowed to occur. In most situations there will be no difficulty in meeting these objectives since, for most fluids, the shear wave energy is dissipated in a few hundredths of a millimeter. Where there is particulate matter mixed in with a fluid base to form fluid 11, the particulate matter can act to alter the fluid viscosity but will not cause significant scattering of the shear waves if the wavelength of these waves is quite long compared to the particulate matter dimensions, the usual situation.

The output voltage appearing at output terminal 14, dependent upon the modulated acoustic energy in piezoelectric transformer 10 as modulated by fluid 11, provides a signal which is a representation of the viscosity of the fluid at the resonance frequency. If piezoeletric transformer 10 is submerged in two different calibrating fluids, i.e. the calibrating fluid is substituted for the fluid of interest 11, or placed in a vacuum and in a calibrating fluid the output voltage at terminal 14 can be related to the known fluid parameters of the selected calibrating fluids. When fluid of interest 11 surrounds piezoelectric transformer 10, the change in output voltage at terminal 14 from the voltage output in a vacuum is a signal which is representative of the viscosity. The transformer output voltage at terminal 14, being stepped-up within the transformer from the input driving voltage at terminals 13, results in an output signal requiring no or very little amplification before further processing of the signal.

This voltage difference signal is not directly proportional to viscosity since other fluid parameters also affect this voltage difference. Thus, these other parameters must be determined for portions of the fluid which are substantially similar to those portions adjacent to piezoelectric transformer 10 that are subjected to the shear waves caused thereby to affect the transformer vibrational characteristics. The representations of these other fluid parameters must also be transmitted to electronics 17 if computational capabilities in electronics 17 are to be used to provide a display which reads out viscosity directly. Of course, the output signal provided to electronics 17 by piezoelectric transformer 10, if not to be subjected to operations within electronics 17, may provide data for reduction by use of external methods and means.

Such computation or reduction operations on the voltage signal appearing at output 14, or upon the voltage difference between this voltage signal and the calibrating voltage signal, must be made for even the simplest of viscous fluids, those fluids exhibiting Newtonian behavior. First, viscosity is known to be always a strong function of fluid temperature, in whatever kind of fluid and so the output voltage at output terminal 14 must also be a function of temperature. Thus, the temperature of the calibrating fluid must be accurately known as must be the temperature of the fluid of interest in those portions thereof adjacent to piezoelectric transformer 10 or in substantially similar fluid portions. This allows correlating the output voltage measurements in both the calibrating fluid and in the fluid of interest 11, and so the fluid viscosities thereof, with temperature.

The voltage at output terminal 14 is also known to be a function of one further fluid parameter in the case of Newtonian fluids, that parameter being fluid density. This relationship can be drived by considering only the mechanical behavior of the piezoelectric transformer and the fluid surrounding it (ignoring temperature). For strictly Newtonian fluids, when the piezoelectric transformer is considered to be a rectangular bar so thin that no shear occurs in the piezoelectric material itself, when any longitudinal waves being generated are neglected, when the shear waves imparted to the fluid encounter no foreign object before dissipation thereof, and when a one dimensional analysis is made, the following relationship results:

$$V_v - V = KV \left[ \frac{\eta \rho}{f_o} \right]^{1/2}$$

$\eta$ = fluid viscosity of fluid of interest
$\rho$ = fluid density of fluid of interest
$f_o$ = resonant frequency in fluid of interest
$V_v$ = output voltage in vacuum
$V$ = output voltage in fluid of interest
$K$ = calibration constant If the density of the fluid is variable, this relationship requires that the density thereof be measured to adjust the voltage output at output terminal 14 for the effects of fluid density.

A correctional computation of the output signal may also be required for the arrangement of FIG. 1 since longitudinal wave energy is, practically, always imparted to a fluid by a vibrating body, but possibly only in negligible amounts. Sufficient radiated longitudinal wave energy imparted to fluid 11 can cause at least two effects which can alter the output voltage signal at terminal 14 of piezoelectric transformer 10 to cause errors in the output signal representation of the apparent viscosity. First, a reactive normal fluid force is exerted on the transformer which, if substantially enough, leads to the generalized radiation impedances of the equivalent electrical circuit having substantial longitudinal wave related resistive and reactive impedance components. These impedance components are not dependent upon fluid parameters, including viscosity, in the same manner as are the impedance components due to shear wave energy and therefore contribute to the output signal in a different manner for the same values of fluid parameters leading to errors therein.

Second, fluids will support longitudinal waves over much greater distances than they will shear waves resulting in possible longitudinal wave reflections causing longitudinal waves to reappear at the surface of the vibrating transformer. Impingement and reflection of longitudinal waves from the surface of the vibrating transformer gives rise to shear effects at this surface and to longitudinal effects at this surface. Both of these kinds of effects again lead to an altered output voltage signal at output terminal 14 and to erroneous results.

If the arrangement of FIG. 1 is such that no substantial reflections of longitudinal waves reach the piezoelectric transformer 10, it is feasible to calculate a correction factor for the output signal voltage due to longitudinal wave energy radiation from the transformer without the substantial complications introduced by reflected waves. This correctional factor can be applied to the output voltage signal from output terminal 14 in electronics 17 or through data reduction methods carried on exclusive of electronics 17 to correct the output signal value to give a proper reading of apparent viscosity. In other situations, either a theoretical or an empirical correctional factor possibly may be determined and this can be applied to the output voltage signal from output terminal 14 for correction thereof.

This viscosimeter measures the point fluid viscosity of non-Newtonian fluids for the particular shear stress applied. If the relationship characterizing the non-Newtonian behavioral aspects of the fluids is known, either theoretically or empirically for the fluid of interest, this information and further fluid parameter measurements pertaining thereto may be used to adjust the voltage signal appearing at output terminal 14 to provide a determination of the Newtonian viscosity parameter as well as the other pertinent parameters. In any event, for a non-Newtonian fluid, the viscosity of the fluid can be provided as a function of the applied shearing stress by varying the magnitude of the driving voltage applied to the input terminals 13 of piezoelectric transformer 10, using the preceding equation to provide the product of fluid viscosity and fluid density for only the particular shear stress applied.

Because of the reliance on the use of shear wave energy, this viscosimeter is capable of measuring the viscosity of fluids of interest when very little of the fluid is available in the vicinity of piezoelectric transformer 10, for most fluids. The shear waves imparted to the fluid, to permit the fluid to affect the piezoelectric transformer vibratory characteristics, are attenuated in a few hundredths of a millimeter for most fluids of interest as stated above. For fluids covering the transformer to a thickness greater than this attenuation length, viscosity may accurately be measured.

Viscosity can be measured for fluids that are at rest as well as fluids that are flowing by the piezoelectric transformer 10 in many instances since a boundary layer will occur along the transformer wherein the fluid is or nearly is at rest with respect to piezoelectric transformer 10. This boundary layer will for many flows and fluids be of the order of the magnitude or greater than the attenuation distance for the shear waves imparted to the fluid by piezoelectric transformer 10. Because of these boundary layers, turbulent flow of many fluids past piezoelectric transformer 10 will not adversely affect the ability of the viscosimeter to measure the viscosity, at least where the turbulance is not too severe.

The arrangement of FIG. 1 wherein the piezoelectric transformer 10 is completely surrounded by fluid of interest 11 restricts the fluid of interest to being a highly non-conductive fluid unless the secondary portion of the transformer has an insulative material provided thereon. This is so because the conductance of the fluid must not short out the right hand side of piezoelectric transformer 10 between mount 12 and output terminal 14. This arrangement also tends to impart a substantial amount of longitudinal wave energy to the fluid 11 because of the resulting motion of the primary half of piezoelectric transformer 10 when driven through input terminals 11.

Figure 2:
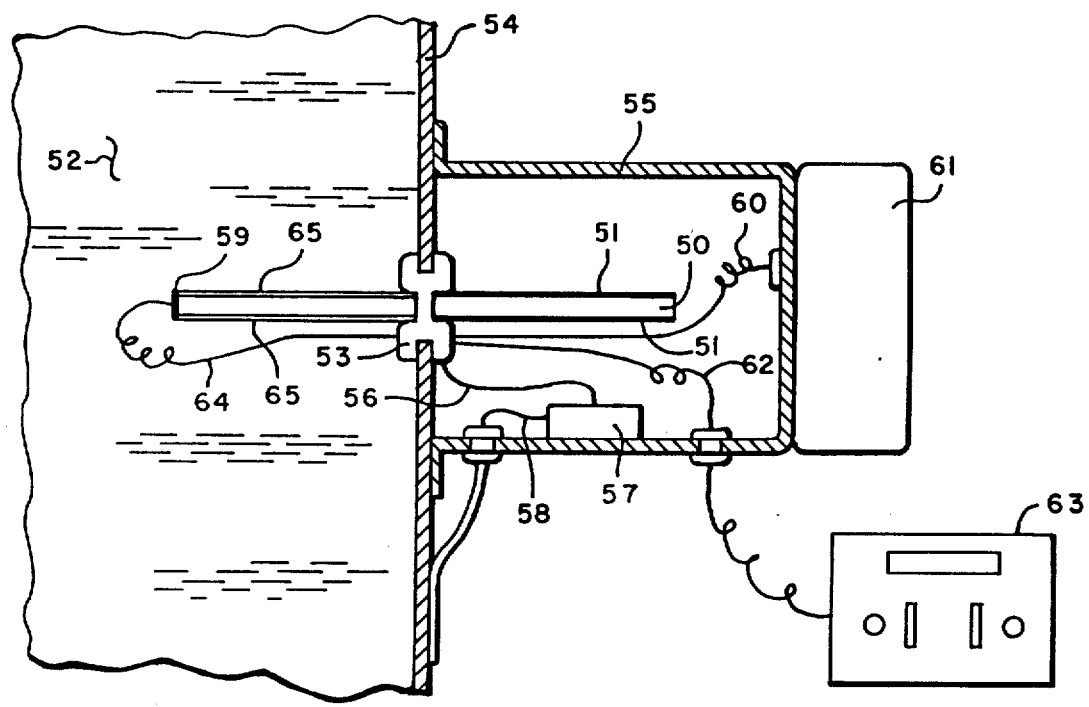
FIG. 2 shows another embodiment of the present invention.

FIG. 2 shows another embodiment of the present invention which permits using a viscosimeter to measure the viscosity of a considerably more conductive fluid of interest and which substantially reduces the longitudinal energy imparted to the fluid 11. In FIG. 2, only that end of the piezoelectric transformer, 50, opposite the end which has the input electrodes, 51, thereon, i.e. the transformer secondary, is provided in the fluid of interest, 52. The remaining half or primary of piezoelectric transformer 50 is outside of fluid 52 beyond the fluid container, 54, and within the protective cover, 55. The transformer is supported in a mount, 53. Cable 56 goes to the driver electronics, 57, which are energized through the power cable, 58. The output terminal, 59, supplies an output voltage signal to cable 64 which is provided through mount 53 to a cable, 60, going to local display electronics 61 and to a cable, 62, going to the remote display and computational electronics, 63. An electrically insulative layer, 65, is provided on the secondary of transformer 50 which may be of sputtered-on quartz if transformer 50 is constructed of PZT, for instance, or a thin plastic film. Such an insulative layer could be provided on the piezoelectric transformer in FIG. 1 also.

Operation of the viscosimeter shown in FIG. 2 parallels that of the viscosimeter shown in FIG. 1 when driver electronics 57 has similar oscillator circuit means. However, whether fluid of interest 52 is conductive or not makes little difference since it comes into contact only with that end of piezoelectric transformer 50 which is insulated by layers 65. When input electrodes 51 are energized, the resulting motion of the secondary of the transformer is a reciprocal, oscillating motion along the direction of elongation of the transformer. This means that the major transformer faces in the secondary move along this same direction of elongation and so nearly impart only shear wave energy to fluid 52. As a result, only the transformer faces having a thickness dimension in them can impart substantial longitudinal wave energy to fluid 52 which can be minimized by reducing this dimension insofar as is practical for a thin piezoelectric transformer.

In this arrangement, the node in the vibratory movement of the transformer will be shifted slightly from the center of the length of piezoelectric transformer 50 because of the unequal loading on the two halves of the piezoelectric transformer. This slight shift will make very little difference in the operation of the viscosimeter, merely adding somewhat to the damping which is effective with respect to the transformer causing some output voltage change from the unshifted node case. The sensitivity of the viscosimeter will be half that of the viscosimeter shown in FIG. 1, however, since the reactive force of fluid of interest 52 will affect only half of the surface area of piezoelectric transformer 50.

A typical situation for the arrangement of FIG. 2 has piezoelectric transformer 50 constructed of lead zirconate titanate with a resonant frequency of approximately 20 kilohertz. By adjusting the input driving voltage amplitude, an output voltage signal level can be selected for the transformer operating in a vacuum or a calibrating fluid. For the output voltage adjusted to 5 volts peak-to-peak in vacuum, the output signal voltage changes by approximately 1 volt when the transformer is submerged in water. There will also be a resonant frequency shift of about 10 hertz.

I claim:

1. A viscosimeter for providing representation of viscosity of a fluid, said viscosimeter comprising:
   a piezoelectric voltage transformer, having electrical terminals thereon serving as input terminals and output terminals, said transformer having surfaces thereof placed in motion in directions in which they are capable of imparting shear waves to those portions of said fluid sufficiently near said surfaces;
   oscillator circuitry means for providing an oscillating electrical voltage at said input terminals; and
   output voltage sensing means which senses an oscillating output voltage signal provided between said output terminals to provide said representation, with oscillations in said output voltage signal occurring at frequencies where said output voltage signal has substantially a maximum amplitude.

2. The system of claim 1 wherein said oscillator circuitry means includes a variable frequency electrical wave generator.

3. The system of claim 1 wherein said oscillator circuitry means includes an oscillator circuit which has said transformer operating as a functional element therein in setting said frequencies at which said oscillator circuitry means oscillates.

4. The system of claim 1 wherein said output voltage sensing means includes computation apparatus.

5. The system of claim 1 wherein any surfaces of said piezoelectric transformer placed in motion in directions in which they are capable of imparting longitudinal wave energy to said fluid have an area sufficiently small so that said longitudinal wave energy imparted to said fluid is so little that said output voltage signal is not influenced substantially thereby.

6. The system of claim 1 wherein a mount supporting said piezoelectric transformer is joined to said piezoelectric transformer at a node in said motion of said surfaces.

7. The system of claim 1 wherein said output voltage sensing means includes display means.

8. The system of claim 1 wherein said piezoelectric transformer is shaped as a rectangular bar and approximately half thereof, excluding surface portions joined to said input terminals, is submerged in said fluid in operation.

9. The system of claim 8 wherein said piezoelectric transformer is completely submerged in said fluid in operation.

10. The system of claim 8 wherein said half submerged has an electrically insulating layer thereon.

11. The system of claim 8 wherein said half puts so little longitudinal acoustic wave energy to said fluid that said output voltage signal is not influenced substantially thereby.

* * * * *